United States Patent
An et al.

(10) Patent No.: US 10,667,760 B2
(45) Date of Patent: Jun. 2, 2020

(54) STIMULATED ECHO SEQUENCE SCANNING MAGNETIC RESONANCE METHOD AND APPARATUS FOR HEART DIFFUSION IMAGING

(71) Applicant: Siemens Healthcare GmbH, Erlangen OT (DE)

(72) Inventors: Jing An, Beijing (CN); Fang Dong, Shenzhen (CN); Zhi Guo Sun, Shenzhen (CN); Yu Yu Wang, Shenzhen (CN); Qiong Zhang, Shenzhen (CN)

(73) Assignee: Siemens Healthcare GmbH, Erlangen (DE)

( * ) Notice: Subject to any disclaimer, the term of this patent is extended or adjusted under 35 U.S.C. 154(b) by 260 days.

(21) Appl. No.: 15/465,976

(22) Filed: Mar. 22, 2017

(65) Prior Publication Data
US 2017/0273638 A1 Sep. 28, 2017

(30) Foreign Application Priority Data
Mar. 22, 2016 (CN) .......................... 2016 1 0164707

(51) Int. Cl.
*A61B 5/00* (2006.01)
*A61B 5/0402* (2006.01)
(Continued)

(52) U.S. Cl.
CPC .......... *A61B 5/7285* (2013.01); *A61B 5/0044* (2013.01); *A61B 5/0402* (2013.01);
(Continued)

(58) Field of Classification Search
CPC ..... A61B 5/7285; A61B 5/055; A61B 5/0402; A61B 5/0044; G01R 33/5635; G01R 33/56341; G01R 33/5673
See application file for complete search history.

(56) References Cited

U.S. PATENT DOCUMENTS 7,941,204 B1 * 5/2011 Wang ................. G01R 33/4824
600/420
8,457,711 B2 * 6/2013 Nezafat .............. G01R 33/5635
600/407
(Continued)

FOREIGN PATENT DOCUMENTS

CN 102008307 A 4/2011
CN 102743172 A 10/2012
(Continued)

OTHER PUBLICATIONS

Huang, Yuqing et al. "Diffusion tensor magnetic resonance imaging for the human heart with free breathing" ISMRM, Proc. Intl. Soc. Mag. Reson. Med. 20, 2012, Abstract #3940.
(Continued)

*Primary Examiner* — Sanjay Cattungal
(74) *Attorney, Agent, or Firm* — Schiff Hardin LLP

(57) ABSTRACT

In a method and magnetic resonance (MR) apparatus for heart diffusion imaging, when an ECG trigger signal by a computer that operates an MR scanner, the MR scanner is operated to acquire a navigator echo before a stimulated echo sequence, in order to detect diaphragm position information. When the first diaphragm position information is not located in an acquisition window, the stimulated echo sequence is not executed, and the computer waits to receive the next ECG trigger signal. The detection time of the navigator echo after the stimulated echo sequence as well as the acquisition time of the stimulated echo sequence, are thus eliminated when the first diaphragm position information does not meet requirements, so can significantly reduce scanning time, and increase the image SNR.

9 Claims, 5 Drawing Sheets

(51) Int. Cl.
*A61B 5/055* (2006.01)
*G01R 33/563* (2006.01)
*G01R 33/567* (2006.01)

(52) U.S. Cl.
CPC .......... *A61B 5/055* (2013.01); *G01R 33/5635* (2013.01); *G01R 33/5673* (2013.01); *G01R 33/56341* (2013.01)

(56) References Cited

U.S. PATENT DOCUMENTS

| | | |
|---|---|---|
| 2002/0087068 A1 | 7/2002 | Foo |
| 2010/0301860 A1* | 12/2010 | Kim .................. G01R 33/4818 324/309 |
| 2011/0044524 A1* | 2/2011 | Wang ..................... G01R 33/54 382/131 |
| 2012/0259202 A1 | 10/2012 | Zheng et al. |
| 2012/0271155 A1 | 10/2012 | Stemmer |
| 2013/0338486 A1 | 12/2013 | Huang |
| 2014/0035577 A1 | 2/2014 | Blumhagen et al. |
| 2014/0285193 A1 | 9/2014 | Huang et al. |
| 2015/0268320 A1 | 9/2015 | Akcakaya et al. |
| 2016/0139225 A1* | 5/2016 | Basha .................... G01R 33/36 324/309 |
| 2017/0038449 A1* | 2/2017 | Voigt .................. G01R 33/4838 |

FOREIGN PATENT DOCUMENTS

| | | |
|---|---|---|
| CN | 102920456 A | 2/2013 |
| CN | 103006217 A | 4/2013 |
| CN | 103479356 A | 1/2014 |
| CN | 103565436 A | 2/2014 |
| WO | 2015162068 A1 | 10/2015 |

OTHER PUBLICATIONS

Nielles-Vallespin, Sonia et al. "In Vivo Diffusion Tensor MRI of the Human Heart: Reproducibility of Breath-Hold and Navigator-Based Approaches" Magnetic Resonance in Medicine, vol. 70, No. 2, pp. 454-465, Aug. 2013 (First Published: Sep. 21, 2012) // https://doi.org/10.1002/mrm.24488.

Ferreira, PF et al. "Improved Navigator Based Diffusion Tensor MRI of the Human Heart in vivo" Journal of Cardiovascular Magnetic Resonance, vol. 15, No. 1, 2013.

Chinese Office Action dated Jan. 14, 2020, for Application No. 201610164707.5.

* cited by examiner

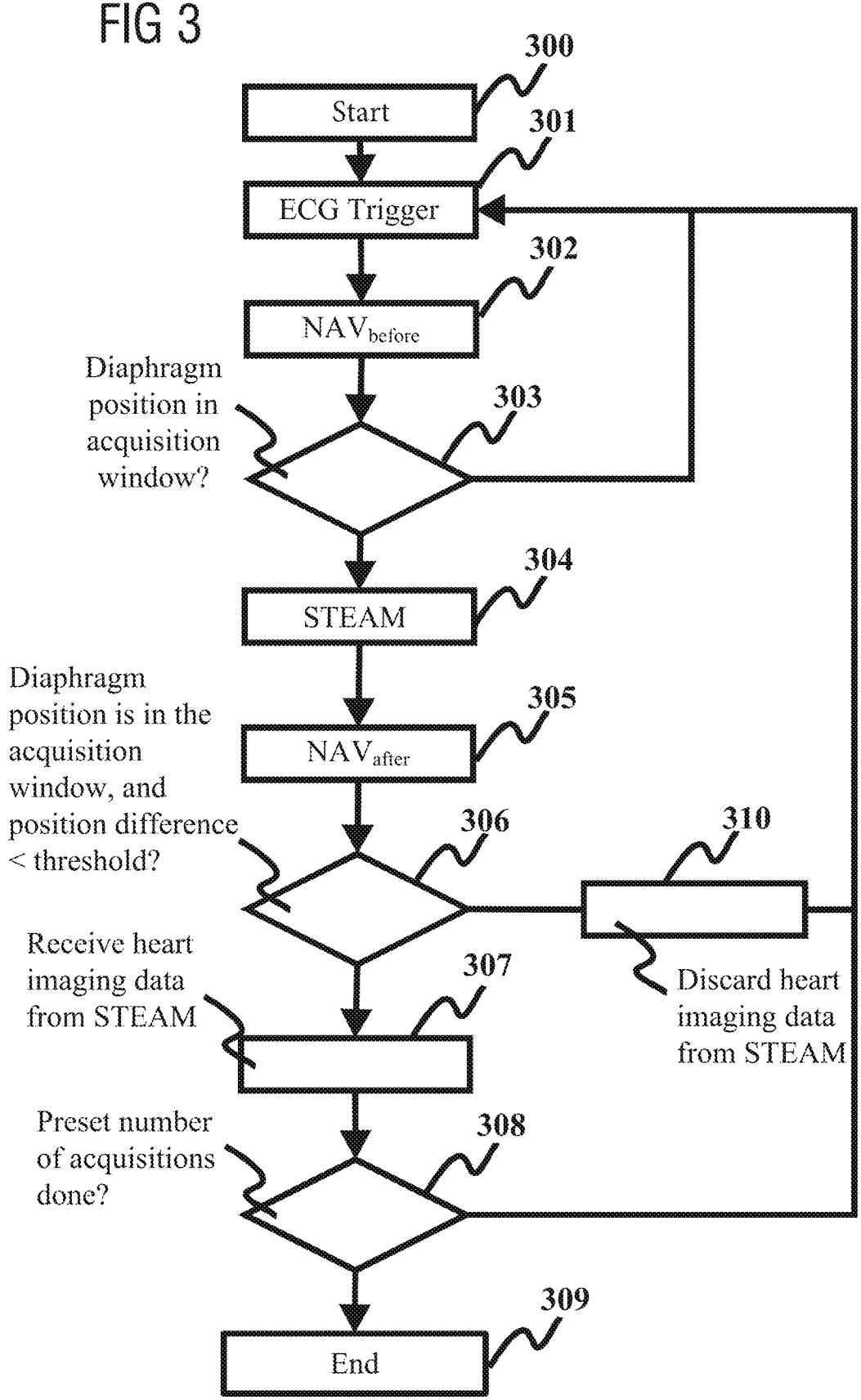

STIMULATED ECHO SEQUENCE SCANNING MAGNETIC RESONANCE METHOD AND APPARATUS FOR HEART DIFFUSION IMAGING

BACKGROUND OF THE INVENTION

Field of the Invention

The present invention concerns the technical field of diffusion imaging, in particular to a stimulated echo magnetic resonance sequence scanning method and apparatus for heart diffusion imaging.

Description of the Prior Art

Magnetic resonance (MR) imaging is an imaging technology involving biomagnetics and nuclear spin which has advanced rapidly with the development of computer technology, electronic circuit technology and superconductor technology. It uses a magnetic field and radio-frequency (RF) pulses to induce oscillation of precessing hydrogen nuclei (i.e. H+) in human tissue, to generate RF signals, which are processed by a computer to form an image.

Diffusion is random, irregular motion of molecules, being one of the ways in which substances are transported in the body, and is also called Brownian motion. The tissue structure of an organism has an effect on the diffusional motion of water molecules therein; conversely, the diffusional motion of water molecules reflects tissue characteristics at the location thereof. Diffusion tensor magnetic resonance imaging (Diffusion Tensor Imaging, DTI) builds upon magnetic resonance imaging (MRI), using non-linear gradient magnetic fields in relevant directions to measure the rate of diffusion of water molecules in tissue in different directions; on this basis, a diffusion tensor of water molecules is calculated, so as to study the fine structure of the interior of tissue.

Diffusion tensor imaging of a living heart can be realized using stimulated echo (STEAM) single-shot echo planar imaging. When diffusion encoding gradients are applied at the same phase in adjacent heartbeat cycles, signal loss due to heart movement can be avoided. To prevent breathing motion from affecting the acquisition process, navigator echoes may be added before and after the STEAM sequence, wherein a navigator band is placed at the top of the diaphragm of the person being scanned.

However, a STEAM scanning method using navigator echoes in the prior art has the drawback of a lengthy scanning time.

SUMMARY OF THE INVENTION

An object of the present invention is to provide propose a stimulated echo sequence scanning method and apparatus for heart diffusion imaging, so as to reduce scanning time.

According to one aspect of the present invention, a stimulated echo sequence scanning method for heart diffusion imaging includes when an ECG trigger signal is received by a control computer, operating an MR scanner with the control computer in order to acquire a navigator echo before a stimulated echo sequence, so as to detect diaphragm position information from a patient in the scanner. If the first diaphragm position information is not located in an acquisition window, the computer does not execute the stimulated echo sequence, and waits to receive the next ECG trigger signal.

In an embodiment, the stimulated echo sequence is executed when the diaphragm position information is located in the acquisition window.

In another embodiment, after executing the stimulated echo sequence, the diaphragm information is first diaphragm information, and a navigator echo is acquired after the stimulated echo sequence in order to detect second diaphragm position information. When the second diaphragm position information is located in the acquisition window and the position difference between the first diaphragm position information and the second diaphragm position information is less than a predetermined threshold, heart imaging data acquired by the stimulated echo sequence are received.

In another embodiment, after the stimulated echo sequence is executed, the method also includes acquiring a navigator echo after the stimulated echo sequence in order to detect second diaphragm position information. When the second diaphragm position information is not located in the acquisition window, heart imaging data acquired by the stimulated echo sequence are discarded.

In a further embodiment, after the stimulated echo sequence is executed, the method also includes acquiring a navigator echo after the stimulated echo sequence to detect second diaphragm position information.

When the position difference between the first diaphragm position information and the second diaphragm position information is not less than a predetermined threshold, heart imaging data acquired by the stimulated echo sequence are discarded.

According to another aspect of the present invention, a stimulated echo sequence scanning apparatus for heart diffusion imaging includes an ECG monitor from which an ECG trigger signal is obtained from a patent. A control computer operates an MR data acquisition scanner to obtain a navigator echo when the ECG trigger signal is received. The navigator echo is acquired before a stimulated echo sequence in order to detect diaphragm position information.

The computer determines when the first diaphragm position information is not located in an acquisition window, and then causes the stimulated echo sequence not to be executed, and waits to receive the next ECG trigger signal.

The computer also causes the stimulated echo sequence to be executed when the diaphragm position information is located in the acquisition window.

In an embodiment, the diaphragm information is first diaphragm information, and the computer is also configured to operate the MR scanner to acquire a navigator echo after the stimulated echo sequence in order to detect second diaphragm position information, when the processing module has executed the stimulated echo sequence.

The computer is also configured to receive heart imaging data acquired by the stimulated echo sequence, when the second diaphragm position information is located in the acquisition window and a position difference between the first diaphragm position information and the second diaphragm position information is less than a predetermined threshold.

In an embodiment, the computer is configured to operate the MR scanner to acquire a navigator echo after the stimulated echo sequence to detect the second diaphragm position information, when the stimulated echo sequence has been executed. The computer discards heart imaging data acquired with the stimulated echo sequence, when the second diaphragm position information is not located in the acquisition window.

In another embodiment, the computer is configured to operate the MR scanner to acquire a navigator echo after the stimulated echo sequence in order to detect the second diaphragm position information, when the stimulated echo sequence has been executed. The computer is also configured to discard heart imaging data acquired by the stimulated echo sequence, when the position difference between the first diaphragm position information and the second diaphragm position information is not less than a predetermined threshold.

In summary in accordance with the present invention, when an ECG trigger signal is received, a navigator echo is acquired before a stimulated echo sequence is enabled, so as to detect diaphragm position information, and when the diaphragm position information is not located in an acquisition window, the stimulated echo sequence is not executed, a wait occurs in order to receive the next ECG trigger signal. If the diaphragm position detected by the navigator echo before the stimulated echo sequence is not located in an acquisition window, it can be assumed that the data that would be acquired by the subsequent stimulated echo sequence would be invalid data, so the subsequent stimulated echo sequence then is not executed in accordance with the present invention, thereby eliminating the acquisition time of that stimulated echo sequence and the detection time of the navigator echo after that stimulated echo sequence, so as to thereby significantly reduce the scanning time.

Moreover, the present invention also lengthens the actual repetition time (TR), so the longitudinal magnetization vector can have sufficient relaxation time, hence the image SNR can also be improved.

BRIEF DESCRIPTION OF THE DRAWINGS

FIG. 3 is a flowchart of a stimulated echo sequence scanning method for heart diffusion imaging according to an embodiment of the present invention.

DESCRIPTION OF THE PREFERRED EMBODIMENTS

The present invention is explained in further detail below in conjunction with the accompanying drawings and embodiments, to clarify the technical solution and advantages thereof. It should be understood that the particular embodiments described here are merely intended to explain the present invention elaboratively, not to define the scope of protection thereof.

The solution of the present invention is explained below by describing a number of representative embodiments, in order to make the description concise and intuitive. The large number of details in the embodiments are merely intended to assist with understanding of the solution of the present invention. The technical solution of the present invention need not be limited to these details when implemented.

Navigator echoes before and after a STEAM sequence are respectively used to detect diaphragm position. The STEAM sequence is used to acquire heart imaging data.

In a STEAM scanning method using navigator echoes in the prior art, navigator echoes before and after the STEAM sequence respectively detect diaphragm position, and the STEAM sequence acquires heart imaging data, then a judgment is made on whether to receive the heart imaging data acquired by the STEAM sequence. A determination is made to receive the heart imaging data acquired by the STEAM sequence only when the diaphragm position detected by the navigator echo before the STEAM sequence complies with requirements, the diaphragm position detected by the navigator echo after the STEAM sequence complies with the requirements, and the value of the difference between the diaphragm position detected by the navigator echo before the STEAM sequence and the diaphragm position detected by the navigator echo after the STEAM sequence complies with requirements.

The invention is based on observational analysis that if the diaphragm position detected by the navigator echo before the STEAM sequence does not comply with requirements, this is sufficient to determine not to receive the heart imaging data acquired by the STEAM sequence; there is no need to perform the work of heart data acquisition by the subsequent STEAM sequence, and no need to perform the work of detection by the navigator echo after the subsequent STEAM sequence. Thus the detection time of the navigator echo after the STEAM sequence and the acquisition time of the STEAM sequence are eliminated, thereby significantly reducing the scanning time.

Figure 1:
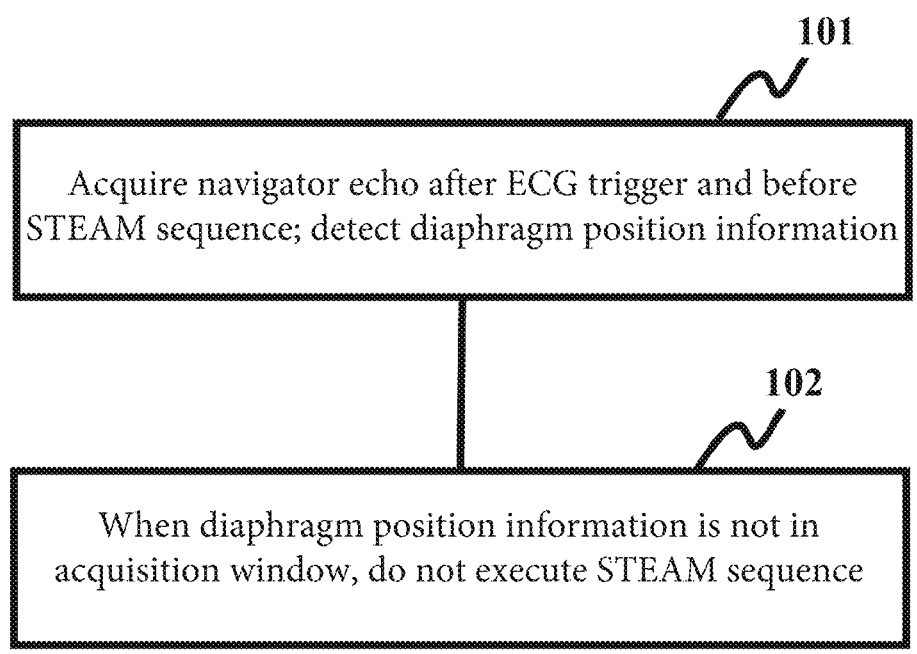
FIG. 1 is a flowchart of a stimulated echo sequence scanning method for heart diffusion imaging according to an embodiment of the present invention.

FIG. 1 is a flowchart of a stimulated echo sequence scanning method for heart diffusion imaging according to an embodiment of the present invention. In this method, navigator echoes are added before and after the STEAM sequence, wherein a navigator band is placed at the top of the diaphragm of the person being scanned. Adding navigator echoes before and after the STEAM sequence can allow the patient to breathe freely during acquisition.

As FIG. 1 shows, the method includes:

Step 101: when an ECG trigger signal is received by a computer that operates an MR scanner, the computer operates the MR scanner to acquire a navigator echo before a STEAM sequence in order to detect diaphragm position information from the navigator echo, from a patient in the MR scanner.

Step 102: when the diaphragm position information is not located in an acquisition window, the STEAM sequence is not executed, and a wait occurs in order to receive the next ECG trigger signal.

After the ECG trigger signal is received and before scanning by the STEAM sequence begins, the navigator echo before the STEAM sequence detects a diaphragm position, to obtain the diaphragm position information. If it is determined that the diaphragm position information is not located in an acquisition window, then it is determined that the data that would be acquired by the subsequent STEAM sequence is invalid data, so the work of heart data acquisition by the subsequent STEAM sequence is not then executed, and the work of detection by the navigator echo after STEAM is not executed. This eliminates the acquisition time of the STEAM sequence and the detection time of the navigator echo after STEAM, and thereby significantly reduces the scanning time.

Furthermore, the present invention also lengthens the actual repetition time, therefore the longitudinal magnetization vector can have sufficient relaxation time, so the signal-to-noise ratio (SNR) of the image can be increased.

In the embodiments of the present invention, when it is determined in step 102 not to execute the STEAM sequence and to wait to receive the next ECG trigger signal, the method shown in FIG. 1 is executed again. This includes, when the STEAM sequence is not executed and after waiting to receive the next ECG trigger signal, continuing to acquire the navigator echo before the STEAM sequence in order to detect diaphragm position information, and when the first diaphragm position information detected this time is still not located in an acquisition window, still not executing the STEAM sequence, but continuing to wait to receive the next ECG trigger signal after the current ECG trigger signal. Extending this principle, if the diaphragm position information detected by the navigator echo before the STEAM sequence is persistently not located in an acquisition window, then the STEAM sequence is persistently not executed.

The method also includes, when the first diaphragm position information is located in an acquisition window, executing the STEAM sequence.

Here, if it is determined that the diaphragm position information is located in an acquisition window, this means that the data that will be acquired by the subsequent STEAM sequence might be valid data, and cannot be immediately discarded, therefore the STEAM sequence is executed, and the STEAM sequence acquires heart imaging data.

In an embodiment, after the STEAM sequence is executed, the diaphragm position information is first diaphragm position information, and the method further includes operating the MR scanner to acquire a navigator echo after the STEAM sequence in order to detect second diaphragm position information, and when a position difference between the first diaphragm position information and the second diaphragm position information is less than a predetermined threshold, receiving heart imaging data acquired by the STEAM sequence.

Here, after the STEAM sequence has been executed because it was determined that the first diaphragm position information detected by the navigator echo before the STEAM sequence was located in an acquisition window, if the second diaphragm position information detected by the navigator echo after the STEAM sequence is likewise located in an acquisition window and the position difference between the first diaphragm position information and the second diaphragm position information is less than the predetermined threshold, this means that the heart imaging data acquired by the STEAM sequence are valid data, therefore the heart imaging data acquired by the STEAM sequence are received by the computer.

In an embodiment, after the STEAM sequence is executed, the method further includes operating the MR scanner to acquire a navigator echo after the STEAM sequence in order to detect second diaphragm position information, and when the second diaphragm position information is not located in an acquisition window, discarding heart imaging data acquired by the STEAM sequence.

Here, after the STEAM sequence has been executed because it was determined that the first diaphragm position information detected by the navigator echo before the STEAM sequence was located in an acquisition window, if it is further determined that the second diaphragm position information detected by the navigator echo after the STEAM sequence is not located in an acquisition window, this means that the data acquired by the STEAM sequence are invalid data. Therefore those data acquired by the STEAM sequence are discarded.

In another embodiment, after the STEAM sequence is executed, the method further includes operating the MR scanner to acquire a navigator echo after the STEAM sequence in order to detect second diaphragm position information, and when a position difference between the first diaphragm position information and the second diaphragm position information is not less than a predetermined threshold, discarding heart imaging data acquired by the STEAM sequence.

Here, after the STEAM sequence has been executed because it was determined that the first diaphragm position information detected by the navigator echo before the STEAM sequence was located in an acquisition window, the navigator echo after the STEAM sequence is acquired in order to detect second diaphragm position information, and if the position difference between the first diaphragm position information and the second diaphragm position information is not less than the predetermined threshold, this means that the data acquired by the STEAM sequence are invalid data. Therefore the data acquired by the STEAM sequence are discarded.

The present invention is explained as an example below in conjunction with a sequence diagram of the STEAM sequence. To prevent breathing motion from affecting the acquisition, navigator echoes are added both before and after the STEAM sequence, wherein a navigator band is placed at the top of the diaphragm of the person being scanned.

Figure 2:
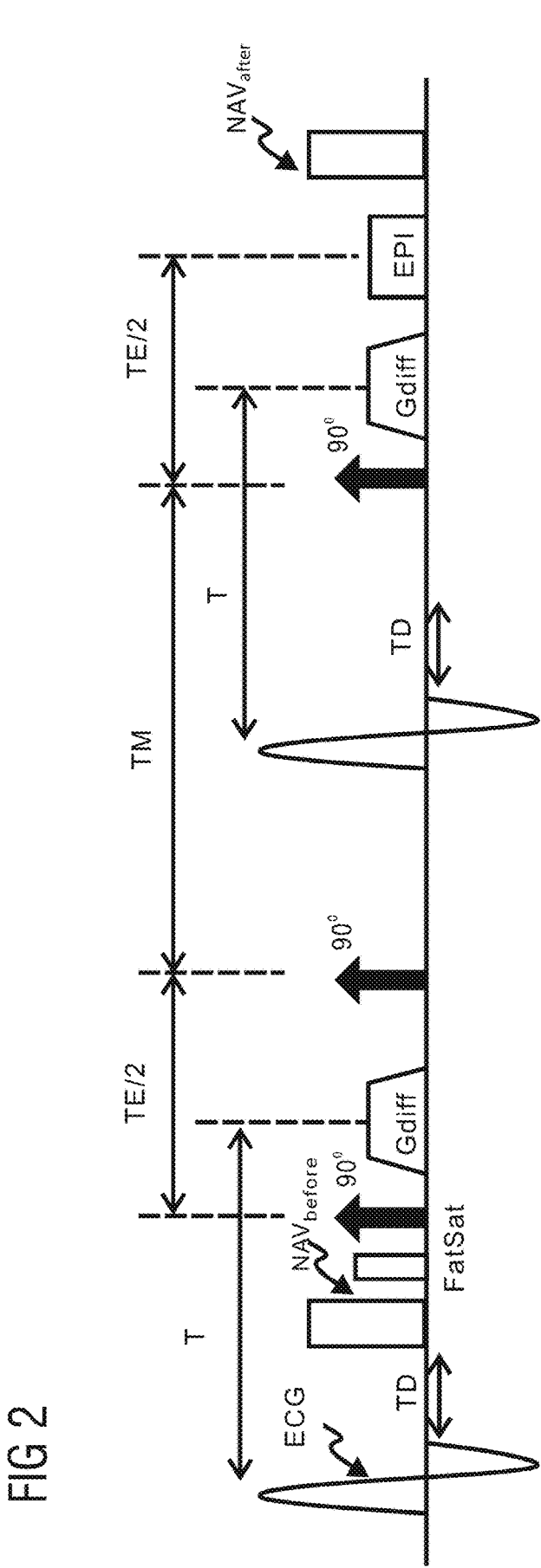
FIG. 2 is a sequence diagram of a stimulated echo (STEAM) sequence with navigator echoes.

FIG. 2 is a sequence diagram of a STEAM sequence with navigator echoes.

In FIG. 2, ECG is an ECG trigger signal; FatSat means fat suppression; Gdiff is diffusion gradient; TD is trigger delay; TE is echo time; TM is mixing or diffusion evolution time; EPI is echo planar imaging.

As FIG. 2 shows, there is a navigator echo before the STEAM sequence ($NAV_{before}$) and a navigator echo after the STEAM sequence ($NAV_{after}$). $NAV_{before}$ is used to detect the diaphragm position at the start of the STEAM sequence; $NAV_{after}$ is used to detect the diaphragm position at the end of the STEAM sequence.

Condition (1): the diaphragm position detected by $NAV_{before}$ must be in an acquisition window (e.g. plus or minus 4 mm);

condition (2): the diaphragm position detected by $NAV_{after}$ must be in an acquisition window (e.g. plus or minus 4 mm);

condition (3): the position difference between the diaphragm position detected by $NAV_{before}$ and the diaphragm position detected by $NAV_{after}$ must be less than a predetermined threshold (e.g. 2 mm).

If any one of the three conditions above is not met, the data acquired by the STEAM sequence must be discarded. In other words, the data acquired by the STEAM sequence are received only if all three of the conditions above are met. Testing experience has demonstrated that when a patient is breathing freely, it is very difficult for these three conditions to be met simultaneously, so the data receiving efficiency is low.

In fact, if condition (1) is not met, then there is no need to perform STEAM sequence acquisition, and there is no need to make a judgment on conditions (2) and (3). Thus, before STEAM sequence scanning starts, once $NAV_{before}$ has detected the diaphragm position, a judgment can be made on condition (1), and if condition (1) is not met, the subsequent STEAM sequence is not then executed.

Specifically, once an ECG trigger signal has been obtained, $NAV_{before}$ acquires diaphragm position information, and a determination is made on whether the diaphragm position information is in an acquisition window; if it is not in an acquisition window, then the STEAM sequence is not executed, but the next ECG signal is awaited, and once diaphragm information has been acquired again, another determination is made on whether condition (1) is met; the STEAM sequence and detection $NAV_{after}$ will only be executed when condition (1) has been met.

Once condition (1) has been met, the STEAM sequence and detection $NAV_{after}$ are executed, and a judgment is made on conditions (2) and (3). Heart imaging data acquired by the STEAM sequence is only received when conditions (2) and (3) are both met. When conditions (2) and (3) cannot both be met, heart imaging data acquired by the STEAM sequence are discarded.

FIG. 3 is a flowchart of a stimulated echo sequence scanning method for heart diffusion imaging according to an embodiment of the present invention.

As FIG. 3 shows, the method includes:

Step 300: start this routine.

Step 301: receive ECG trigger signal.

Step 302: enable navigator echo $NAV_{before}$ to detect diaphragm position.

Step 303: determine whether the diaphragm position detected by the navigator echo $NAV_{before}$ is located in an acquisition window, and if it is, perform step 304 and subsequent steps, otherwise return to step 301.

Step 304: execute the STEAM sequence, which is used to acquire heart imaging data.

Step 305: enable navigator echo $NAV_{after}$ to detect diaphragm position.

Step 306: determine whether the following two conditions are both met: (1) the diaphragm position detected by $NAV_{after}$ is located in an acquisition window; (2) the position difference between the diaphragm position detected by $NAV_{before}$ and the diaphragm position detected by $NAV_{after}$ is less than a predetermined threshold d; if these two conditions are both met, perform step 307 and subsequent steps, and if these two conditions cannot both be met, perform step 310.

Step 307: receive heart imaging data acquired by the STEAM sequence, and increment a preset acquisition variable $N_{image}$ by one.

Step 308: determine whether the acquisition variable $N_{imagine}$ is equal to a preset number of acquisitions n, and if it is, perform step 309, otherwise return to step 301.

Step 309: end this routine.

Step 310: discard the heart imaging data acquired by the STEAM sequence, and return to step 301.

The beneficial effects of the present invention are expounded demonstratively below in conjunction with the accompanying drawings.

Figure 4A:
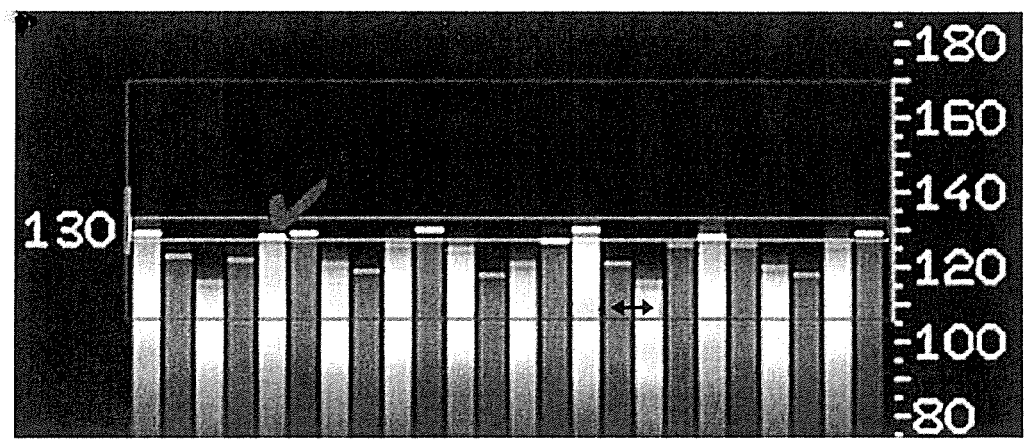
FIG. 4A is a schematic diagram of data reception of a navigator echo in the prior art.
Figure 4B:
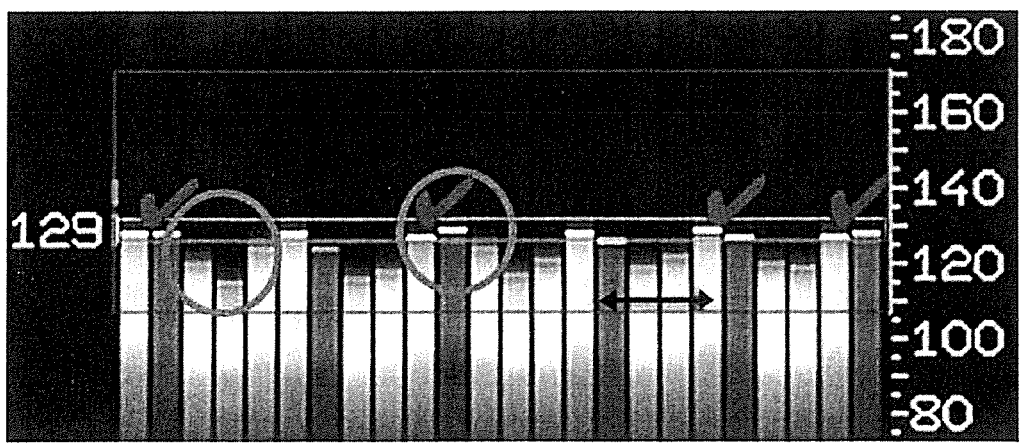
FIG. 4B is a schematic diagram of data reception of a navigator echo according to an embodiment of the present invention.

FIG. 4A is a schematic diagram of data reception by a navigator echo in the prior art; FIG. 4B is a schematic diagram of data receiving by a navigator echo according to an embodiment of the present invention. In FIGS. 4A and 4B, the navigator bands are placed at the top of the diaphragm of the person being scanned.

FIGS. 4A and 4B both show motion of the liver with breathing. In FIGS. 4A and 4B, the black region at the top of the figure corresponds to the lungs; the white column-shaped bars correspond to $NAV_{before}$ detection data; the black column-shaped bars correspond to $NAV_{after}$ detection data. STEAM sequence scanning is performed between white and black column-shaped bars. In FIGS. 4A and 4B, a tick indicates that conditions (1), (2) and (3) have all been met, and acquired data can be received.

Detection $NAV_{after}$ only occurs after the STEAM sequence, so the black column-shaped bars indicate that the STEAM sequence has been executed. The number of black column-shaped bars in FIG. 4B is less than the number of black column-shaped bars in FIG. 4A; this means that the embodiment of the present invention does not perform meaningless STEAM sequence scanning, and therefore saves a great amount of scanning time.

In FIG. 4B, the circle on the left represents inhalation; the circle on the right represents exhalation. It can be seen from FIG. 4B that the white column-shaped bars are repeated continually until a white column-shaped bar falls within an acquisition window. This fall-in position is the beginning of a final phase of exhalation; subsequently, a black column-shaped bar appears, indicating that the STEAM sequence has been executed. If the black column-shaped bar is still in an acquisition window, and the value of the difference between the white column-shaped bar and the black column-shaped bar is less than d (e.g. d is 2 mm), then it can be ensured that the STEAM sequence is executed when breathing motion is small in the final phase of exhalation, and data acquired by the STEAM sequence will be received. Clearly, when the present invention is adopted, $NAV_{before}$ can find the optimal start time of the final phase of exhalation in order to trigger sequence execution, and conditions (2) and (3) are more easily met. Thus, compared with FIG. 4A, the data receiving rate in FIG. 4B is significantly increased.

As shown by the double arrows in FIGS. 4A and 4B, the actual TR is the time between two black column-shaped bars. It can be seen by comparing FIGS. 4A and 4B that the double arrow in FIG. 4B is longer than the double arrow in FIG. 4A; this indicates that the present invention also lengthens the actual repetition time (TR). Thus, when the present invention is applied, the longitudinal magnetization vector can have sufficient relaxation time, so the image has a higher SNR.

Figure 5:
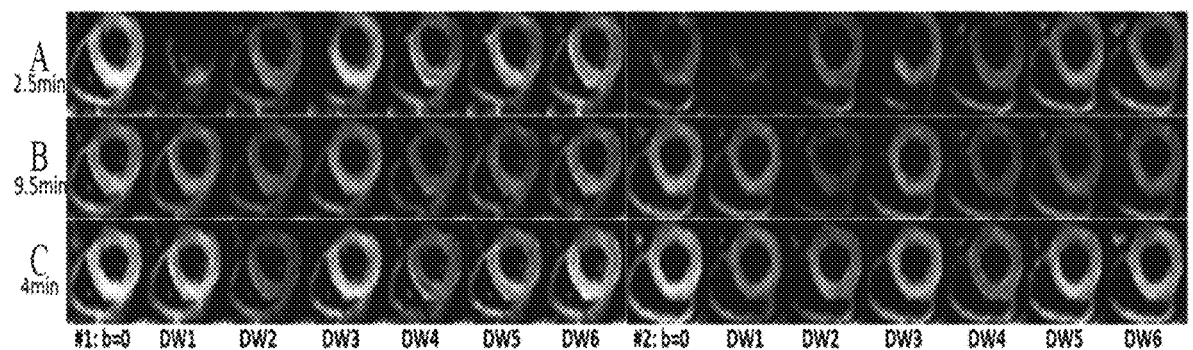
FIG. 5 is a chart comparing the imaging results of the 2D Prospective Acquisition Correction (PACE) method in the prior art, a navigator echo method in the prior art, and an embodiment of the present invention.

The present invention has been realized on the IDEA platform of Siemens, and has been demonstrated in experiments. FIG. 5 is a demonstrative chart comparing the imaging results of the 2D Prospective Acquisition Correction (PACE) method, a navigator echo method in the prior art and the present invention. These three types of scanning sequence are: a PACE scanning sequence; a navigator echo scanning sequence in the prior art; a STEAM ep2d_diff scanning sequence. In these three scanning methods, phase encoding gradients are applied in six directions, the b value is 350 s/mm$^2$, and the number of layers is 4 (short axis position). Furthermore, all of the images obtained by these three methods are presented in the same window-width window position.

In FIG. 5:

The first row (i.e. row A) is scanning results based on PACE. Clearly, the scanning results based on PACE have the drawback of lacking robustness; some of the images have been affected by breathing motion.

The second row (i.e. row B) is scanning results based on navigator echoes in the prior art. The scanning method based on navigator echoes in the prior art has the drawback of a long scanning time, so is not suitable for clinical use. Moreover, the scanning results based on navigator echoes in the prior art have the drawback of a low image SNR. This is because the actual TR is 2 RR intervals, and the longitudinal magnetization vector does not have sufficient relaxation time.

The third row (i.e. row C) is scanning results of an embodiment of the present invention. Clearly, the present invention improves upon the scanning method based on navigator echoes in the prior art; while maintaining good robustness, it also shortens the scanning time (e.g. it may reduce it by half), and the image SNR is also significantly improved.

Table 1 shows the results of comparing navigator echoes based on PACE and the prior art with navigator echoes in the present invention.

TABLE 1

|  | SNR | Robustness | Efficiency | Comfort |
| --- | --- | --- | --- | --- |
| PACE | + | − | ++ | + |
| Navigator echoes in prior art | − | + | − | + |
| Navigator echoes in present invention | + | + | + | + |

It can be seen from table 1 that in the PACE scheme: the SNR is good, robustness is poor, efficiency is excellent, and comfort is good; in the navigator echo scheme in the prior art:

the SNR is poor, robustness is good, efficiency is poor, and comfort is good. In the embodiment of the present invention: the SNR is good, robustness is good, efficiency is good, and comfort is good.

Clearly, compared with the PACE scheme and the navigator echo scheme in the prior art, the present invention simultaneously guarantees SNR, robustness, excellent efficiency, and comfort.

Figure 6:
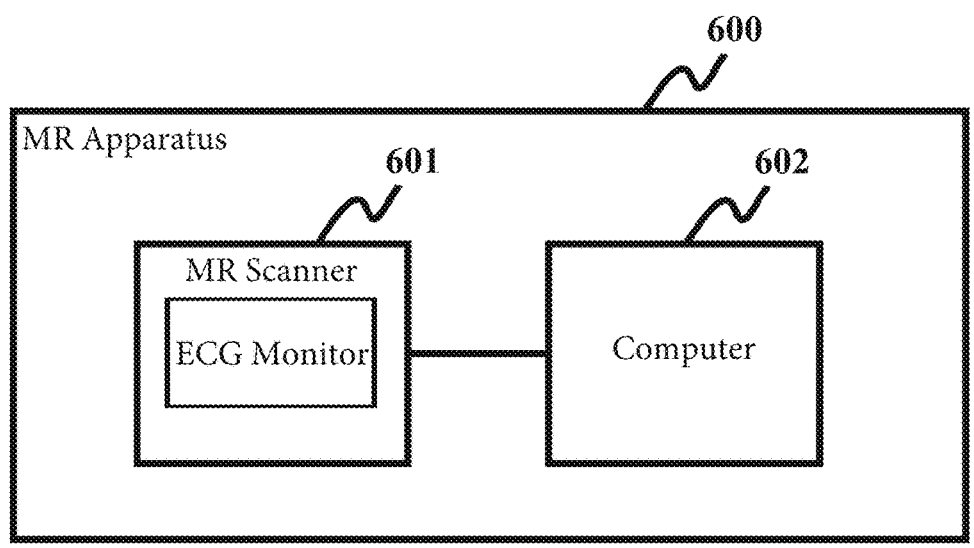
FIG. 6 is schematic illustration of a stimulated echo sequence scanning apparatus for heart diffusion imaging according to an embodiment of the present invention.

FIG. 6 is a block diagram of a stimulated echo sequence scanning apparatus for heart diffusion imaging according to an embodiment of the present invention.

As FIG. 6 shows, the MR apparatus 600 includes an MR scanner 601 operated by a computer 602. The MR scanner 601 includes an ECG monitor 603 adapted for connection to a patient (not shown) in the MR scanner 601, in order to obtain an ECG trigger signal, which is supplied to the computer 602. The computer 602 operates the MR scanner 601, when an ECG trigger signal is received, in order to acquire a navigator echo, before operating the MR scanner 601 to execute a stimulated echo sequence. Diaphragm position information are obtained in the computer 602 from the navigator echo. When this diaphragm position information is not located within an acquisition window, the computer 602 causes the MR scanner 601 to not execute the stimulated echo sequence, and the computer 602 waits to receive the next ECG signal.

In one embodiment, the computer 602 is also confirmed to execute the stimulated echo sequence when the diaphragm position information is located in the acquisition window.

In an embodiment the diaphragm position information is first diaphragm position information, and the MR scanner 601 is also operated by the computer 602 to acquire a navigator echo after the stimulated echo sequence, in order to detect second diaphragm position information, when the scanner 601 has executed the stimulated echo sequence, the computer 602 receives heart imaging data acquired by the stimulated echo sequence, when the second diaphragm position information is located in an acquisition window and the position difference between the first diaphragm position information and the second diaphragm position information is less than a predetermined threshold.

In another embodiment, the MR scanner 601 is also operated by the computer 602 to acquire a navigator echo after the stimulated echo sequence in order to detect second diaphragm position information, when the scanner 601 has executed the stimulated echo sequence. The computer 602 discards heart imaging data acquired by the stimulated echo sequence, when the second diaphragm position information is not located in an acquisition window.

In another embodiment, MR scanner 601 is operated by the computer 602 to acquire a navigator echo after the stimulated echo sequence in order to detect second diaphragm position information, when the MR scanner 601 has executed the stimulated echo sequence. The computer 602 discards heart imaging data acquired by the stimulated echo sequence, when the position difference between the first diaphragm position information and the second diaphragm position information is not less than a predetermined threshold.

In order to implement the inventive method, the computer 602 has a non-transitory, computer-readable data storage medium loaded therein, which is encoded with programming instructions (program code). The programming instructions cause the computer 602 to implement the inventive method when the programming instructions are executed therein.

The storage medium may be, but is not limited to: floppy disk, optical disk, DVD, hard disk, flash memory, etc.

Furthermore, the stimulated echo sequence scanning method for heart diffusion imaging in the embodiments of the present invention may also be applied in storage media based on flash memory (Nand flash), such as USB stick, CF card, SD card, SDHC card, MMC card, SM card, memory stick, xD card, etc.

In summary in accordance with the present invention, when an ECG trigger signal is received, a navigator echo is acquired before a stimulated echo sequence is enabled, so as to detect diaphragm position information, and when the diaphragm position information is not located in an acquisition window, the stimulated echo sequence is not executed, a wait occurs in order to receive the next ECG trigger signal. If the diaphragm position detected by the navigator echo before the stimulated echo sequence is not located in an acquisition window, it can be assumed that the data that would be acquired by the subsequent stimulated echo sequence would be invalid data, so the subsequent stimulated echo sequence then is not executed in accordance with the present invention, thereby eliminating the acquisition time of that stimulated echo sequence and the detection time of the navigator echo after that stimulated echo sequence, so as to thereby significantly reduce the scanning time.

Moreover, the present invention also lengthens the actual repetition time, so the longitudinal magnetization vector can have sufficient relaxation time, hence the image SNR can also be improved. In addition, compared with the PACE scheme and the navigator echo scheme in the prior art, the present invention simultaneously guarantees SNR, robustness, excellent efficiency, and comfort.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for operating a magnetic resonance (MR) apparatus, comprising:

providing a computer with an electrocardiogram (ECG) signal obtained from a subject in an MR scanner, said computer being configured to operate the MR scanner to execute a stimulated echo sequence in order to acquire MR data from the subject for heart diffusion imaging;

in said computer, identifying an ECG trigger signal in said ECG signal and, upon identification of said ECG trigger signal, operating the MR scanner to acquire a navigator echo from the patient, in order to detect first diaphragm position information therefrom, before operating said MR scanner to execute said stimulated echo sequence;

in said computer, identifying whether said first diaphragm position information is located in an acquisition window and, when said first diaphragm position information is not located in said acquisition window, not operating said MR scanner to execute said stimulated echo sequence, and waiting to identify a next ECG trigger signal;

when said first diaphragm position information is within said acquisition window, emitting electronic control signals from said computer to said MR scanner that cause said MR scanner to execute said stimulated echo sequence, after said MR scanner executes said stimulated echo sequence:
  from said computer, operating said MR scanner to acquire a navigator echo to detect second diaphragm information;
  in said computer, identifying (i) whether said second diaphragm position information is within said acquisition window, and (ii) a position difference between said first diaphragm position information and said second diaphragm position information;
  in said computer, comparing said position difference to a predetermined threshold; and
  in said computer, when (i) said second diaphragm position information is within said acquisition window, and (ii) said position difference is less than said predetermined threshold, receiving heart imaging data from said MR scanner acquired by the execution of said stimulated echo sequence.

2. A method as claimed in claim 1, further comprising, after said MR scanner executes said stimulated echo sequence:
in said computer, when said second diaphragm position information is not within said acquisition window, discarding heart imaging data acquired by the MR scanner with said stimulated echo sequence.

3. A method as claimed in claim 1, further comprising, after said MR scanner executes said stimulated echo sequence:
in said computer, when said position difference is not less than said predetermined threshold, discarding heart imaging data acquired by said MR scanner with said stimulated echo sequence.

4. The method as claimed in claim 1, wherein the acquisition window is defined in accordance with a range of the diaphragm position over time.

5. The method as claimed in claim 4, wherein the predetermined threshold has a value that is less than the range of the diaphragm position.

6. The method as claimed in claim 1, wherein the value of the predetermined threshold is associated with a range of the diaphragm position during a final phase of exhalation.

7. A magnetic resonance (MR) apparatus comprising:
an MR scanner;
an electrocardiogram (ECG) monitor adapted for connection to a patient in the MR scanner in order to obtain an ECG signal from the patient;
a computer provided with the ECG signal obtained from the subject in the MR scanner, said computer being configured to operate the MR scanner to execute a stimulated echo sequence in order to acquire MR data from the subject for heart diffusion imaging;
said computer being configured to identify an ECG trigger signal in said ECG signal and, upon identification of said ECG trigger signal, said computer being configured to operate the MR scanner to acquire a navigator echo from the patient, in order to detect first diaphragm position information therefrom, before operating said MR scanner to execute said stimulated echo sequence; and
said computer being configured to identify whether said first diaphragm position information is located in an acquisition window and, when said first diaphragm position information is not located in said acquisition window, to not operate said MR scanner to execute said stimulated echo sequence, and to wait to identify a next ECG trigger signal,
wherein said computer is configured, when said first diaphragm position information is within said acquisition window, to emit electronic control signals from said computer to said MR scanner that cause said MR scanner to execute said stimulated echo sequence,
said computer is configured to, after said MR scanner executes said stimulated echo sequence:
  operate said MR scanner to acquire a navigator echo to detect second diaphragm information;
  identify (i) whether said second diaphragm position information is within said acquisition window, and (ii) a position difference between said first diaphragm position information and said second diaphragm position information;
  compare said position difference to a predetermined threshold;
  when (i) said second diaphragm position information is within said acquisition window, and (ii) said position difference is less than said predetermined threshold, to receive heart imaging data from said MR scanner acquired by the execution of said stimulated echo sequence.

8. An MR apparatus as claimed in claim 7, wherein said computer is configured,
when said second diaphragm position information is not within said acquisition window, to discard heart imaging data acquired by the MR scanner with said stimulated echo sequence.

9. An MR apparatus as claimed in claim 7, wherein said computer is configured,
when said position difference is not less than said predetermined threshold, to discard heart imaging data acquired by said MR scanner with said stimulated echo sequence.

* * * * *